United States Patent [19]

Setälä

[11] Patent Number: 4,565,806

[45] Date of Patent: Jan. 21, 1986

[54] COMPOSITION AND METHOD FOR RATIONAL TREATMENT OF CANCER

[76] Inventor: Kai M. E. Setälä, Uimarinpolku 10 B, 00330 Helsinki 33, Finland

[21] Appl. No.: 609,475

[22] Filed: May 11, 1984

Related U.S. Application Data

[63] Continuation-in-part of Ser. No. 293,973, Aug. 18, 1981.

[51] Int. Cl.[4] .................. A61K 31/715; A61K 31/725; A61K 31/66; A61K 31/505
[52] U.S. Cl. ........................................ 514/54; 514/56; 514/110; 514/256; 514/288; 514/554; 514/708; 514/731; 514/936
[58] Field of Search .................. 568/27; 424/183, 261, 424/251, 315, 316, 324, 337; 514/54, 56, 110, 256, 288, 554, 708, 731, 936

[56] References Cited

PUBLICATIONS

Hill, "A Review of Cyclophosphamide", C. Thomas Pub. Chapt. 9., pp. 242-273, 1975.
Crethman et al., The Pharmacological Basis of Therapy, 6th ed., McMillan Inc., p. 1364, 1980.
Cecil Textbook of Medicine, 1979, pp. 1931, 1932, 1934, 1935 and 1936.
Setälä, A Rational Anti-Cancer Therapy Experimental Study in Mice, Med. Sci., 9:1117-1118, 1981.
K. Setälä, Med. Hypothesis, 8:207-230, 1982.
Warren et al., "Potentiation of Anti Neoplastic Compounds, NY Acad. Sci. 243:194-208, 1975.

*Primary Examiner*—Albert T. Meyers
*Assistant Examiner*—John W. Rollins, Jr.
*Attorney, Agent, or Firm*—Toren, McGeady, Stanger, Goldberg & Kiel

[57] ABSTRACT

The invention concerns a composition, i.e., a multifunctional medically active agent for rational therapy of malignant (cancerous) diseases based on cause-and-effect relationship. The new composition according to the invention contains dimethylsulfoxide, DMSO, or sulfolan, preferably DMSO, in combination with a therapeutically effective amount of at least one cytostatic agent. The invention also concerns a method for treatment of malignant (cancerous) conditions in man comprising local or systemic administration thereto of an effective dosage of the composition according to the invention.

The invention surprisingly provides a composition, as well as a method of treatment, allowing rational specific or selective carcinostatic-carcinocidic therapy. This therapy-form aims at the intracytoplasmic 3-dimensional cytoskeleton (differentiation organelle) that is specifically changed in the malignant cells, as well as at the targets responsible for karyokinesis and cytokinesis.

5 Claims, No Drawings

COMPOSITION AND METHOD FOR RATIONAL TREATMENT OF CANCER

CROSS-REFERENCE TO RELATED APPLICATIONS

This application is a continuation-in-part of copending application Ser. No. 293,973, filed Aug. 18, 1981, the contents of which are incorporated herein by reference.

BACKGROUND OF THE INVENTION

The individual observations forming the background for the invention emanate from large-scale animal experiments on mice, however in which solely human drugs (cytostatics) were used which all are already familiar and applied in clinical practice in the USA. A cytostatic usually denotes a drug that affects the proliferating capacity of the cells by its inhibitory action of DNA, RNA or protein biosynthesis in general; sometimes these drugs are called antiproliferative or cytostatic agents, or mitotic poisons.

It is recognized that malignant diseases form an important category among diseases in general, being without adequate therapy in particular. All presently used cytostatics are, firstly nonspecific, and secondly, toxic. Although all medically active agents possess toxic properties, the applicable dosage range between the therapeutic dose and the toxic dose of the cytostatic is extremely narrow and the margin of error slight. Furthermore, administration of a cytostatic to the host may have profound effects on host defences, altering the delicate balance which may exist between host and tumor. As a consequence, suppression of host defences may not only facilitate cancerous progression, but may render the host more susceptible to infectious complications by pathogenic micro-organisms.

The desired result of chemotherapy of cancer is death of the cancerous cells, with destruction of the latter and sparing of viability and functions of the normal cells. These drugs, when administered to the tumor-bearer, simultaneously inhibit biochemical sites that are not unique to cancerous cells. Hence, the present cytostatics simultaneously kill or injure severely normal cells as well.

Most fateful for the design of the present-day anticancer drugs has been the generally accepted hypothesis according to which it should be granted that normal cells and cancerous cells have the same biosynthetic and regulatory mechanisms, and that cancer cells respond to a given anticancer agent in the same manner as do the normal homologous cells. In other words, if proliferating normal cells are injured by a noxious agent, it is postulated that the same holds true of cancerous cells.

In the following are given some of the experimental observations on mice which form the fundament for the invention. It appeared surprisingly that when separate observations, seemingly independent, were arranged in a purposeful order in relation to each other, the resulting constellation showed a new specific pathway for design of a rational anticancer therapy. These observations are in short:

(1) One of the most decisive prerequisites in general has been the use of mouse strains with known inborn (congenital) neoplastic potentialities, i.e., the ability to develop tumors. For the studies on which the present invention is based, results from experiments with female mice of the skin-tumor-resistant RA strain were used.-(Sette,uml/a/ lä, K (Editor) "Visualization of dormant cellular features in mouse epidermia correlated with skin tumor evolution." Acta Path Microbiol Scand Suppl 155 (1961)). Setälä, Kai "Defective cell maturation, an alternative to accelerated cell division as target for cancer therapy", Progress in Experimental Tumor Research, Vol 5, p. 1 (1964).

(2) For the detection of delicate events or patterns in cell differentiation, keratinization of the epidermal cells was used as exponent for differentiation.

(3) The benign epidermal condition—generally called the stage of tumor promotion in experimental cancer research provoked by the known tumor promoter Tween 60 ® (polyoxyethylene sorbitan monostearate) and the malignant counterpart provoked by the carcinogen 9,10-dimethyl-1,2-benzanthracene (DMBA) are in all respects opposite to each other (Setälä, Kai "Relation of benign and malignant epidermal hyperplasia in mouse", Proc. I Int. Conf. Univ. Perugia p. 529 (1962). Large-scale experiments have been performed. Parallel studies comprised tumor-production series, light, polarization and electron microscopy, histochemical and histoquantitative examination, and in vitro analyses on various mixed lipo/protein surface films. The total animal material now comprises about 30,000 mice with varying degrees of inherited susceptibility towards skin-tumor formation. In samples taken from 1,800 mice, 930,000 karyokinetic assemblies and 14,522,600 corresponding nucleated nondividing cells from various conditions of the epidermis were analyzed.

(4) It has been convenient to use relative high doses (nearby maximal doses allowed) of cytostatics for evaluation of their effects upon the target. However, to be able to detect delicate patterns in the target tissue, the dose of the cytostatic has to be as low and nondestructive as possible to avoid the disturbing development of mass injury, which would otherwise have masked subtle differences in the modes of response. This has been the guideline. For final evaluation, doses of cytostatics were selected which do not cause at all, or only in an infinitesimal degree, changes in the malignant (cancerous) condition, but in contrast cause strong effects in the normal target emanating from the same tissue of origin. (Setälä, Kai "Differences in pharmacodynamic response to colchicine between benign and malignant epidermal hyperplasia" Acta Radiol. Suppl 237 (1965)). (Setälä, K "Konträre pharmakodynamische Antwortsweise der gutartigen und kanzerösen Epidermishyperplasie der RA Mäuse auf das onkolytische Alkaloid Vinca rosae Linn. "Naturwissenschaften Vol 52, p. 564 (1965).

(5) To reveal the degree and mode of effect of a given cytostatic, experiments were needed utilizing side-by-side three different targets: the benign (hyperplastic) condition, the malignant (cancerous) condition, and the normal tissue of origin, the epidermis.

(6) The results on which the new anticancer strategy and the composition of the invention are based were obtained in experiments in which 8 different known cytostatic agents were separately utilized. These were: the archetype mitotic poison, colchicine; vinblastine sulfate; phlorizin; triethylene thiophosphamide; sodium chloride of cyclophosphamide; humic acid (polymetic component of soil humus); fluorouracil; and SP-J-Sandoz.

(7) the results from experiments performed with the drugs given above show—among other things—that the normal epidermis and the benign (hyperplastic) epidermal condition are extremely susceptible to the effects of the subtreshold doses of the 8 cytostatics tested. Thus, even a dose of 60 gamma per day of the drug, given only once, provoked a vigorous response: a high number of pathological mitotic figures, and of epidermal "monster cells". The type of the karyokinetic injury was that characterized as pre-prophase-poisoning syndrome. In contrast, the malignant (cancerous) condition was extremely nonresponsive, almost indolent to the same cytostatic under related experimental circumstances. In addition, the karyokinetic disturbance did not reveal any pre-prophase-poisoning type otherwise characteristic of cytostatics in general. All 8 cytostatics tested revealed related results. Because at that time it was not possible to evaluate the final character of the nonresponsiveness of the malignant cells, the property was called "cytoplasmic barrier" of the malignant cells towards the effects of cytostatics.

(8) The results further revealed that the karyokinetic activity in the malignant (carcinogen-provoked) epidermal condition is significantly lower than that in the benign (hyperplastic, tumor promoter-provoked) epidermal condition. It was furthermore shown that the characteristic of the cancerous epidermal cells is thus not an intense cell proliferation rate, but in contrast a delayed and misguided cell differentiation (maturation) (Setälä, K et al. "Verlängerte Lebensdauer der Tochterzellen bzw. herabgesetzte Mitoserate der Basalzellen als Ausdruck des Carcinogeneffektes in Mäuseepidermis". Naturwissenschaften Vol 48, p. 673 (1961)).

(9) Following the observations made above under (7) and (8), it was recommended that the delayed and misguided cell differentation (maturation) should be used as a target for the design of a specific anticancer strategy, and not solely principles which should interfere with the karyokinetic activity only.

(10) Experimental result showed clearly that it is in fact possible to lower the degree of malignancy of the cancerous epidermal cells by forcing them to proceed towards re-differentiation. These observation further indicate that it is possible to arrest the malignant progression—at an experimental level—even by several different and fairly simple methods. Among these therapeutic attempts was utilization of adenosene triphosphate ATP, together with the tumor promoting substance Tween 60 ® (with its two-phase properties) while ATP served as the energy source (Setälä, Kai et al., "Input of energy compelling carcinogen injured epidermal cells in mice to proceed with differentiation" Naturwissenschaften vol 48 p. 225 (1961)).

Further, the steroid cholesterol was beneficially utilized because of its role at and effects on the cell surface membrane (Setälä, Kai et al. "Inhibitory action of cholesterol addition to Tween 60 ® on the tumor promoting and epidermal hyperplasia causing effects in mouse skin" Naturwissenschaften vol 46, p. 331 (1959)). This observation was later applied by other investigators. Furthermore, Tween 60 ® was used because of its hydrating (two-phase) and membrane-active properties, and urea in Tween 60 ® (Setälä, Kai et al. "Inhibition of evolution of multiple skin tumours in mice. A simple technique based on cause and effect relationships", Multiple Primary Malignant Tumours (L. Severi, ed.) Perugia (1973) p. 393) because of its known alfa-helix-rupturing properties which increase the availability of "free" water molecules in the cells.

(11) However, a feature of cardinal importance is the intracytoplasmic 3-dimensional cytoskeleton composed of molecular chains - the cytodifferentiation organelle (in epidermal cells, keratinization organelle) detected by us 20 years ago. It is particular organelle that should be the target for anticancer attacks. Further, the existence of and changes in this organelle for the first time allows a direct insight into the mechanism underlying (experimental) skin carcinogenesis in mice.

Examination of sections cut serially at right angles to each other showed that the cells contain an intracytoplasmic 3-dimensional basket-like cytoskeleton. This is partly arranged around the nucleus, which the most peripheral parts of it are closely connected with paramembraneous structures and, partly, with the corresponding patterns of the adjacent cells. Cytodifferentiation occurs within this organelle. In the malignant cells, the organelle is deranged, rigid and—partly—increased in mass, while the cancerous cells are dehydrated. The presence of this differentiation organelle was first detected in epidermal cells (cf references on page 3, lines 1 to 7 and Setälä, K et al., "Input of energy compelling carcinogen injured epidermal cells in mice to proceed with differentiation" Naturwissenschaften vol 48 p. 225 (1961)). Setälä, K et al., "Mechanism of experimental tumorigenesis. 9. Sulphydryl groups, disulphide bonds, and birefringence in mouse epidermis after exposure to dipole-type tumor promoter and carcinogen" Acta Path. Microbiol. Scand. Vol 54, p. 39 (1962)). Thereafter the existence of the organelle has been confirmed and shown to exist in all eukaryotic mammalian cells.

(12) It has been shown that—under experimental circumstances—the carcinogen and the cytostatic act largely on the same target: both cause severe alterations in the 3-dimensional cytoskeleton. Hence, therapeutic exposures of the cancerous cells to a cytostatic means that the drug focuses its effects on a target already hardened by exposure to a carcinogen. This observation may explain the reason why the carcinogen-provoked malignant epidermal cells possess the "cytoplasmic barrier" against the effect of after-treatment with a cytostatic.

(13) It has suddenly and surprisingly now became evident that dimethylsulfoxide, DMSO, focuses its effects just towards the intracytoplasmic 3-dimensional cytoskeleton. In normal cells and in benign (hyperplastic) cells the cytoskeleton remains unchanged after exposure of the cell to DMSO (the same is true as to Tween 60 ®). In contrast the cytoskeleton of malignant (cancerous) cells becomes stabilized (dispersed) by the effect of DMSO exposure.

(14) the peculiar properties of DMSO may explain the reason why the cytoskeleton (composed of protein belonging to the actin-myosin-/actomyosin/-epidermin-fibrinogen group) of the malignant cells can so easily be stabilized. According to the literature on DMSO, this polar substance (the first hydrating substance utilized, Tween 60 ® is nonpolar-polar in nature) as a molecule behaves like a zwitterion having an electrostatic charge density on its oxygen atom comparable to that of the fluoride ion. Further, the DMSO anion interacts with water to form an A-region having two water molecules, i.e. a DMSO. $2H_2O$ complex. Additional studies on various biopolymers show that DMSO. $2H_2O$ complex helps to stabilize the helix structure of its target(s). DMSO is said to exist as a resonance hybrid having strong protein dispersing power. In other words, DMSO alters the configuration and water-binding capacity of proteins and other vital biopolymers, increasing their flexibility and looseness.

(15) As stated under (7) above, when the normal epidermis and the benign (hyperplastic) epidermal condition and the malignant (carcinogen-provoked) condition were topically exposed to the effects of the 8 cytostatics studied (only one cytostatic in each series), the normal cells and the cells of the benign hyperplasia responded extremely vigorously although the dose of the cytostatic was of a subthreshold order only. A high incidence of pathological cell division figures developed; further a high incidence of epidermal "monster cells" occurred. The volume of the cytoplasm increased mani-fold (up to 20-fold). The intracytoplasmic 3-dimensional cytoskeleton became unmasked. The cystatic-dependent alterations were evident already after 24 hours after a single exposure. In these two targets the changes were reversible and showed after 72 h a distinct tendency to recover. Addition of DMSO to the cytostatic-solution does not essentially alter the mode and degree of response.

In contrast, the mode and strength of the response of the malignant condition differed fundamentally from the above. Thus, in series without DMSO addition, the response was very weak or at places non-existent, only a very low incidence of epidermal "monster cells" developed. The intracellular vacuolization was of low degree, the size of the malignant cells did not essentially increase. The 3-dimensional cytoskeleton was only slightly altered. But, when the same cytostatic was administered in the presence of DMSO, the situation changed in a highly significant manner. Now the reaction was extremely vigorous and resembled in principle that seen in normal cells and the cells of benign (hyperplastic) condition. A high number of pathological mitotic figures developed, similarly now even epidermal "monster cells" occurred. Statistical analyses based on histoquantitative examination revelated that the differences between related parameter-pairs were highly significant ($p < 0.001$) in all series. Light, polarization and electron microscopy strengthened the statistical observations. The cytostatic-DMSO-provoked changes in the malignant (cancerous) condition were irreversible.

DESCRIPTION OF THE INVENTION

The composition for treatment of cancer thus contains on the one hand an agent, which possesses both hydrating and oxidation-reduction properties (preferably DMSO), and on the other, a known cytostatic, i.e. a drug that affects the proliferating capacity of cells by its inhibitory action of DNA, RNA, or protein biosynthesis in general.

According to the present invention, the new anticancer strategy leads,—through vigorous rehydration and morbid swelling of the cytoplasm of the malignant cells—to (a) a high-degree dilution of the cytoplasm and to (b) rupture of the fibers and breakdown of the characteristically dehydrated, rigid, hardened and deranged intracytoplasmic 3-dimensional cytoskeleton composed of fibers and filaments (the cyto-differentiation organelle). The death of the malignant cells as a result of the treatment of the invention depends at least on two separate events, being partly due to injurious effects of over-imbition with water of the cells (whereby the volume of the malignant cells increase 20-fold or even more), and partly because the subthreshold doses of the cytostatic carried by the hydrating agent can exert its desired effects better in the highly rehydrated intracellular water matrix in which the cytoskeleton thus has been collapsed. In contrast, the normal and hyperplastic (benign) cells of the same tissue of origin are not irreversibly attacked by the composition. Therefore, application of the proposed new composition for cancer therapy represents a rather selective mode of treatment. Most important from the standpoint of the invention, depending on the peculiar properties of DMSO and on the observed linearity of the ratio dose of the cytostatic / severity of the resulting changes in the target, the therapeutic dosage of the cytostatic administered in cancer therapy can be decreased in a highly significant manner, down to from 1/10 to 1/100 of the dosage conventionally used clinically. It is stipulated that it might be possible to decrease the dose even further, down to 1/1,000 of the conventional. Consequently, two alternative courses are possible: either the efficacy of the cytostatic can be increased in a highly significant manner in the presence of the hydrating agent; or in the presence of the hydrating agent, the dose of the same cytostatic can be decreased, e.g., to 1/100. Applying the new anticancer strategy of the present invention, the dose of the cytostatic is reduced to a "safe" level that would spare the viability and functions of the normal cells: the risk of untoward side-effects of the said cytostatic is minimized.

Instead of DMSO, sulfolan can be used although DMSO is in all respects superior for the proposed purpose.

As a cytostatic agent may, for this purpose known cytostatic agents can be used, e.g. the above mentioned colchicine, vinblastine sulfate, phloridzin, triethylene thiophosphamide, humic acid, fluorouracil, nitrogen mustards, e.g. cyclophosphamide, mechlorethamine.

The dosage of cytostatic administered naturally depends on i.a. the nature and severity of the cancerous condition to be treated and the frequency of administration, but according to the invention the dosage of cytostatic, when used together with the hydrating agent e.g. DMSO, can be reduced to at least 1/10-1/100 of the conventionally administered dosages. The dosage levels and the frequency of administration presently used also vary with the specific cytostatic used and are known to those skilled in the art. As examples the following conventional dosages may be mentioned

| cytostatic agent | Conventional dosage according to Cecil Textbook of Medicine, PB Beason, W. McDermott, IB Wyngaarden; Saunders, Philadelphia, London, Toronto 1979. | |
|---|---|---|
| Vinblastine sulfate | 0.1–0.5 mg/kg/week i.v. | |
| Fluorouracil | 12 mg/kg/day iv | (initially; for 4 days) |
| | 10–15 mg/kg/week iv | upkeep |
| Cyclophosphamide | 10–20 mg/kg/day iv | (for 2–5 days; totally 40–50 mg/kg |
| Mechlorethamine | 0.4 mg/kg/i.v. | single dose |

According to the invention the dosages mentioned above may thus be reduced to 1/10–1/100 when combined with the hydrating agent, preferably DMSO.

Thus, when combined with DMSO the dosage of vinblastine sulfate can be reduced to 0.001–0.05 mg/week/kg iv, that of flurorouracil to 0.2–1.2 mg/day/kg iv for initial treatment and to 0.10–0.5 mg/week/kg iv.for upkeep, that of cyclophosphamide to 0.1–2.0 mg/day/kg i.v. and that of mechloretamine to 0.004–0.04 mg/kg body weight i.v.

The amount of DMSO used is not critical and varies with the mode of application (local or systemic). A suitable amount for a single dose can be e.g. 10 ml when administered by injection.

Further, instead of using only one cytostatic in the composition, two or even more could be used, in combination. Hereby the most advantageous method is to utilize cytostatics with differing desired effects.

Instead of or in addition to cytostatics, a number of other specifical noxious agents can be added to the hydrating agent. Among these are, e.g., known (natural or synthetic) substances interfering with transformations in the cellular sol-gel balance (among these particularly clotting vs. anticlotting principles already applied in clinical practice, such as heparin or dicoumarol). The hydrating agent could further contain agents that exert their effects directly towards the 3-dimensional malignantly altered cytoskeleton (among these are certain specifically adapted proteolytic vs. fibrinolytic enzyme systems, ontained, e.g., from Aspergillus orycae). Even appropriately prepared immunological principles could be included which attack the 3-dimensional cytoskeleton in an irreversible manner.

Depending on the physicochemical and chemical properties of DMSO, and on all that what is known about its carrier and other properties in the living environment, the simplest mode of preparation of the anticancer composition is to dissolve the desired amount of cytostatics in a suitable amount of DMSO. DMSO maintains the solute, i.e., when administered to a living target, the cytostatic follows DMSO.

I claim:

1. A method of treatment of skin cancer in man comprising percutaneous or intravenous administration thereto of an effective dosage of a composition comprising in combination dimethylsulfoxide and a therepeutically effective subthreshold dose of a cytostatic agent selected from the group consisting of colchicine, vinblastine sulfate, phloridzin, triethylene thiophosphamide, cyclophosphamide, humic acid, fluorouracil and mechlorethamine.

2. The method of claim 1 wherein vinblastine sulfate is used in a dosage of 0.001–0.05 mg/week/kg body weight i.v.

3. The method of claim 1 wherein fluorouracil is used in an initial dosage of 0.12–1.2 mg/day/kg body weight i.v.

4. The method of claim 1 wherein cyclophosphamide is used in a dosage of 0.1–2.0 mg/day/kg body weight i.v.

5. The method of claim 1 wherein mechlorethamine is used in a dosage of 0.004–0.04 mg/kg body weight i.v.

* * * * *